(12) United States Patent
Stacchino et al.

(10) Patent No.: US 7,857,845 B2
(45) Date of Patent: Dec. 28, 2010

(54) CARDIAC-VALVE PROSTHESIS

(75) Inventors: Carla Stacchino, Turin (IT); Giovanni Bergamasco, Turin (IT); Gaetano Burriesci, London (GB); Giovanni Righini, Chivasso (IT)

(73) Assignee: Sorin Biomedica Cardio S.R.L., Saluggia (Vercelli) (IT)

( * ) Notice: Subject to any disclaimer, the term of this patent is extended or adjusted under 35 U.S.C. 154(b) by 192 days.

(21) Appl. No.: 11/352,021

(22) Filed: Feb. 10, 2006

(65) Prior Publication Data

US 2006/0178740 A1    Aug. 10, 2006

(30) Foreign Application Priority Data

Feb. 10, 2005    (IT) .......................... TO2005A0074

(51) Int. Cl.
*A61F 2/24*    (2006.01)
(52) U.S. Cl. ..................... 623/2.17; 623/2.18
(58) Field of Classification Search ....... 623/2.36–2.42, 623/1.24–1.26, 2.14–2.18; *A61F 2/24*
See application file for complete search history.

(56) References Cited

U.S. PATENT DOCUMENTS

| | | | |
|---|---|---|---|
| 3,657,744 A | 4/1972 | Ersek | |
| 3,671,979 A | 6/1972 | Moulopoulos | |
| 3,997,923 A | 12/1976 | Possis | |
| 4,056,854 A | 11/1977 | Boretos et al. | |
| 4,086,665 A | 5/1978 | Poirier | |
| 4,451,936 A * | 6/1984 | Carpentier et al. | 623/2.4 |
| 4,477,930 A | 10/1984 | Totten et al. | |
| 4,506,394 A | 3/1985 | Bedard | |
| 4,692,164 A | 9/1987 | Dzemeshkevich et al. | |

(Continued)

FOREIGN PATENT DOCUMENTS

DE    195 46 692 C2    6/1997

(Continued)

OTHER PUBLICATIONS

European Search Report issued in EP App No. 08165227, dated Mar. 13, 2009, 7 pages.

(Continued)

*Primary Examiner*—William H. Matthews
*Assistant Examiner*—Jason-Dennis Stewart
(74) *Attorney, Agent, or Firm*—Faegre & Benson LLP

(57) ABSTRACT

A cardiac-valve prosthesis which can be used, for example, as a valve for percutaneous implantation. The prosthesis includes an armature for anchorage of the valve prosthesis in the implantation site. The armature defines a lumen for passage of the blood flow and supports a set of prosthetic valve leaflets, which, under the action of the blood flow, are able to move into a radially divaricated condition to enable the flow of the blood through the lumen in a first direction and a radially contracted condition, in which the valve leaflets co-operate with one another and block the flow of the blood through the prosthesis in the opposite direction. The armature includes, in one embodiment, two annular elements connected by anchor members having the capacity of projecting radially with respect to the prosthesis, and support members for the set of leaflets, the support members being carried by at least one of the annular elements so as to leave substantially disengaged the aforesaid lumen for passage of the blood.

19 Claims, 6 Drawing Sheets

U.S. PATENT DOCUMENTS

| | | |
|---|---|---|
| 4,758,151 A | 7/1988 | Arru et al. |
| 4,777,951 A | 10/1988 | Cribier et al. |
| 4,994,077 A | 2/1991 | Dobben |
| 5,084,151 A | 1/1992 | Vallana et al. |
| 5,123,919 A | 6/1992 | Sauter et al. |
| 5,133,845 A | 7/1992 | Vallana et al. |
| 5,139,515 A | 8/1992 | Robicsek |
| 5,314,468 A | 5/1994 | Martinez et al. |
| 5,332,402 A | 7/1994 | Teitelbaum |
| 5,370,685 A | 12/1994 | Stevens |
| 5,387,247 A | 2/1995 | Vallana et al. |
| 5,397,351 A | 3/1995 | Pavcnik et al. |
| 5,411,552 A | 5/1995 | Andersen et al. |
| 5,423,886 A | 6/1995 | Arru et al. |
| 5,545,214 A | 8/1996 | Stevens |
| 5,545,215 A | 8/1996 | Duran |
| 5,554,185 A | 9/1996 | Block et al. |
| 5,712,953 A | 1/1998 | Langs |
| 5,716,417 A | 2/1998 | Girard et al. |
| 5,824,037 A | 10/1998 | Fogarty et al. |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,876,436 A | 3/1999 | Vanney et al. |
| 5,891,195 A | 4/1999 | Klostermeyer et al. |
| 5,925,063 A | 7/1999 | Khosravi |
| 5,954,766 A | 9/1999 | Zadno-Azizi et al. |
| 5,957,949 A | 9/1999 | Leonhardt et al. |
| 5,980,570 A | 11/1999 | Simpson |
| 6,162,245 A | 12/2000 | Jayaraman |
| 6,168,614 B1 | 1/2001 | Andersen et al. |
| 6,197,143 B1 | 3/2001 | Bodnar |
| 6,245,102 B1 | 6/2001 | Jayaraman |
| 6,270,526 B1 | 8/2001 | Cox |
| 6,299,638 B1 | 10/2001 | Sauter |
| 6,309,417 B1 | 10/2001 | Spence et al. |
| 6,312,462 B1 | 11/2001 | McDermott et al. |
| 6,352,554 B2 | 3/2002 | De Paulis |
| 6,402,780 B2 | 6/2002 | Williamson, IV et al. |
| 6,425,916 B1 | 7/2002 | Garrison et al. |
| 6,440,164 B1 | 8/2002 | DeMatteo et al. |
| 6,454,799 B1 | 9/2002 | Schreck |
| 6,458,153 B1 | 10/2002 | Bailey et al. |
| 6,482,228 B1 | 11/2002 | Norred |
| 6,494,909 B2 | 12/2002 | Greenhalgh |
| 6,544,285 B1 | 4/2003 | Thubrikar et al. |
| 6,569,196 B1 | 5/2003 | Vesely |
| 6,582,462 B1 | 6/2003 | Andersen et al. |
| 6,652,578 B2 | 11/2003 | Bailey et al. |
| 6,656,219 B1 | 12/2003 | Wiktor |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,790,230 B2 | 9/2004 | Beyersdorf et al. |
| 6,805,711 B2 | 10/2004 | Quijano et al. |
| 6,830,584 B1 | 12/2004 | Seguin |
| 6,830,585 B1 | 12/2004 | Artof et al. |
| 6,875,231 B2 | 4/2005 | Anduiza et al. |
| 6,929,653 B2 | 8/2005 | Strecter |
| 7,018,404 B2 | 3/2006 | Holmberg et al. |
| 7,125,418 B2 | 10/2006 | Duran et al. |
| 7,175,656 B2 | 2/2007 | Khairkhahan |
| 7,186,265 B2 | 3/2007 | Sharkawy et al. |
| 7,211,107 B2 | 5/2007 | Bruckheime |
| 7,252,682 B2 | 8/2007 | Seguin |
| 7,255,706 B2 | 8/2007 | Rosengart |
| 7,261,732 B2 | 8/2007 | Justino |
| 7,276,078 B2 | 10/2007 | Spenser et al. |
| 7,329,278 B2 | 2/2008 | Seguin et al. |
| 7,329,279 B2 | 2/2008 | Haug et al. |
| 7,347,869 B2 | 3/2008 | Hojeibane et al. |
| 7,351,256 B2 | 4/2008 | Hojeibane et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,393,360 B2 | 7/2008 | Spenser et al. |
| 7,534,259 B2 | 5/2009 | Lashinski et al. |
| 7,556,645 B2 | 7/2009 | Lashinski et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 * | 11/2009 | Case et al. ................. 623/1.26 |
| 7,708,775 B2 | 5/2010 | Rowe et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0039450 A1 | 11/2001 | Pavcnik et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0123802 A1 | 9/2002 | Snyders |
| 2002/0128702 A1 | 9/2002 | Menz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0055495 A1 | 3/2003 | Pease et al. |
| 2003/0109924 A1 | 6/2003 | Cribier |
| 2003/0130729 A1 | 7/2003 | Paniagua et al. |
| 2003/0149476 A1 | 8/2003 | Damm et al. |
| 2003/0153974 A1 | 8/2003 | Spenser et al. |
| 2003/0163194 A1 | 8/2003 | Quijano et al. |
| 2003/0191528 A1 | 10/2003 | Quijano et al. |
| 2003/0208261 A1 | 11/2003 | Thorpe et al. |
| 2004/0034407 A1 * | 2/2004 | Sherry ....................... 623/1.15 |
| 2004/0034411 A1 | 2/2004 | Quijano et al. |
| 2004/0039436 A1 | 2/2004 | Spenser et al. |
| 2004/0049266 A1 | 3/2004 | Anduiza et al. |
| 2004/0055606 A1 | 3/2004 | Hendricksen et al. |
| 2004/0078072 A1 | 4/2004 | Tu et al. |
| 2004/0078074 A1 | 4/2004 | Anderson et al. |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0106976 A1 | 6/2004 | Bailey et al. |
| 2004/0260389 A1 | 12/2004 | Case et al. |
| 2005/0010285 A1 | 1/2005 | Lambrecht et al. |
| 2005/0033398 A1 | 2/2005 | Seguin |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 * | 4/2005 | Bergheim ................. 623/1.26 |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |

| | | |
|---|---|---|
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0197695 A1 | 9/2005 | Stacchino et al. |
| 2005/0222675 A1 | 10/2005 | Sauter |
| 2005/0234546 A1* | 10/2005 | Nugent et al. ............. 623/2.11 |
| 2005/0261759 A1 | 11/2005 | Lambrecht et al. |
| 2006/0085060 A1 | 4/2006 | Campbell |
| 2006/0178740 A1 | 8/2006 | Stacchino et al. |
| 2006/0190017 A1 | 8/2006 | Cyr et al. |
| 2006/0195184 A1 | 8/2006 | Lane et al. |
| 2006/0259137 A1 | 11/2006 | Artof et al. |
| 2007/0032850 A1* | 2/2007 | Ruiz et al. ................. 623/1.11 |
| 2007/0093887 A1 | 4/2007 | Case et al. |
| 2007/0093890 A1 | 4/2007 | Eliasen et al. |
| 2007/0100432 A1 | 5/2007 | Case et al. |
| 2007/0100435 A1 | 5/2007 | Case et al. |
| 2007/0100440 A1 | 5/2007 | Figulla et al. |
| 2007/0106372 A1 | 5/2007 | Osborne et al. |
| 2007/0118209 A1 | 5/2007 | Strecker |
| 2007/0118215 A1 | 5/2007 | Moaddeb |
| 2007/0168024 A1 | 7/2007 | Khairkhahan |
| 2007/0185513 A1 | 8/2007 | Woolfson et al. |
| 2007/0233228 A1 | 10/2007 | Eberhardt et al. |
| 2007/0237802 A1 | 10/2007 | McKay et al. |
| 2007/0239265 A1 | 10/2007 | Birdsall et al. |
| 2007/0239273 A1 | 10/2007 | Allen |
| 2007/0244544 A1 | 10/2007 | Birdsall et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0293942 A1 | 12/2007 | Mirzaee |
| 2008/0065204 A1 | 3/2008 | Macoviak et al. |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0125859 A1 | 5/2008 | Salahieh et al. |
| 2008/0133033 A1 | 6/2008 | Wolff et al. |
| 2008/0188880 A1 | 8/2008 | Fischer et al. |
| 2008/0228263 A1 | 9/2008 | Ryan |
| 2009/0157175 A1 | 6/2009 | Benichou et al. |
| 2009/0164006 A1 | 6/2009 | Seguin et al. |
| 2009/0171456 A1 | 7/2009 | Kveen et al. |
| 2009/0209955 A1 | 8/2009 | Forster et al. |
| 2009/0210052 A1 | 8/2009 | Forster et al. |
| 2009/0222082 A1 | 9/2009 | Lock et al. |
| 2009/0222084 A1 | 9/2009 | Friedman |
| 2009/0254165 A1 | 10/2009 | Tabor et al. |

FOREIGN PATENT DOCUMENTS

| | | |
|---|---|---|
| DE | 198 57 887 A1 | 7/2000 |
| EP | 0 133 420 B1 | 2/1988 |
| EP | 0 155 245 B1 | 5/1990 |
| EP | 0 592 410 B1 | 10/1995 |
| EP | 0 850 607 A1 | 7/1998 |
| EP | 1 057 460 A1 | 12/2000 |
| EP | 1 088 529 A2 | 4/2001 |
| EP | 1 259 194 B1 | 2/2005 |
| EP | 1 214 020 B1 | 3/2005 |
| EP | 2 055 266 A2 | 5/2005 |
| EP | 1 570 809 A1 | 9/2005 |
| EP | 1 014 896 B1 | 11/2005 |
| EP | 1 603 493 A2 | 12/2005 |
| EP | 1 600 127 B1 | 11/2006 |
| EP | 1 143 882 B1 | 5/2007 |
| EP | 1 330 213 B1 | 3/2009 |
| EP | 1 370 201 B1 | 9/2009 |
| EP | 2 133 039 A1 | 12/2009 |
| NL | 1 017 275 | 8/2002 |
| WO | WO 97/24989 | 7/1997 |
| WO | WO 98/17202 | 4/1998 |
| WO | WO 98/29057 | 7/1998 |
| WO | WO 99/13802 A1 | 3/1999 |
| WO | WO 99/56665 | 11/1999 |
| WO | WO 00/41852 | 7/2000 |
| WO | WO 00/47139 | 8/2000 |
| WO | WO 00/62714 | 10/2000 |
| WO | WO 00/62716 | 10/2000 |
| WO | WO 01/21107 A1 | 3/2001 |
| WO | WO 01/62189 A1 | 8/2001 |
| WO | WO 01/64137 A1 | 9/2001 |
| WO | WO 01/76510 A2 | 10/2001 |
| WO | WO 02/41789 A2 | 5/2002 |
| WO | WO 02/047575 A2 | 8/2002 |
| WO | WO 02/078348 A1 | 10/2002 |
| WO | WO 03/003943 A2 | 1/2003 |
| WO | WO 03/003949 A2 | 1/2003 |
| WO | WO 03/094797 A1 | 11/2003 |
| WO | WO 2004/082527 A2 | 9/2004 |
| WO | WO 2004/091455 A2 | 10/2004 |
| WO | WO 2005/046528 A1 | 5/2005 |
| WO | WO 2006/044679 A1 | 4/2006 |
| WO | WO 2006/086135 A | 8/2006 |
| WO | WO 2009/029199 A1 | 3/2009 |

OTHER PUBLICATIONS

European Search Report issued in EP Application No. 06101425, dated May 3, 2006, 6 pages.

European Search Report issued in EP Application No. 08150075, dated Mar. 27, 2008, 6 pages.

* cited by examiner

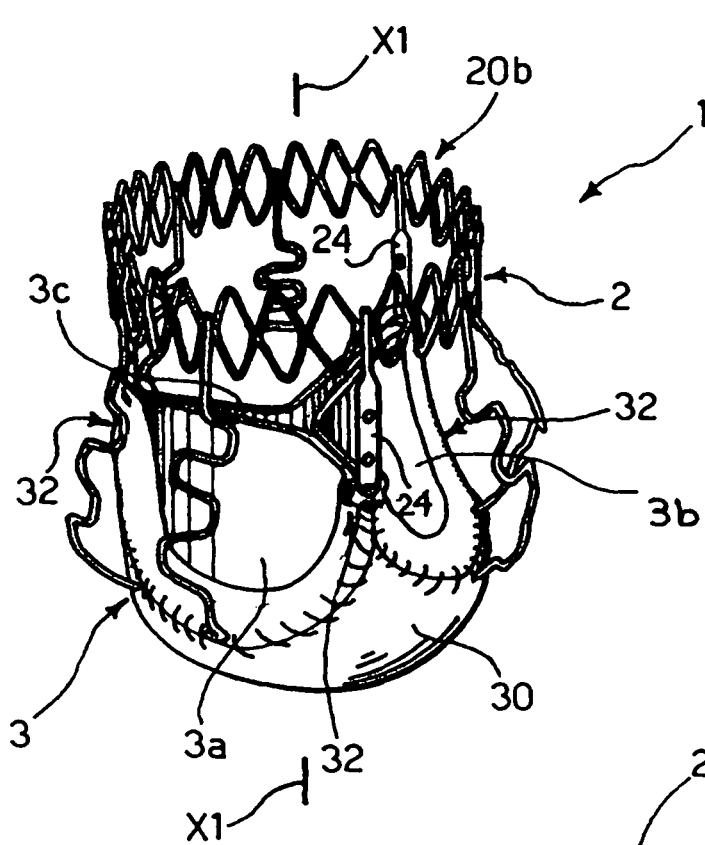
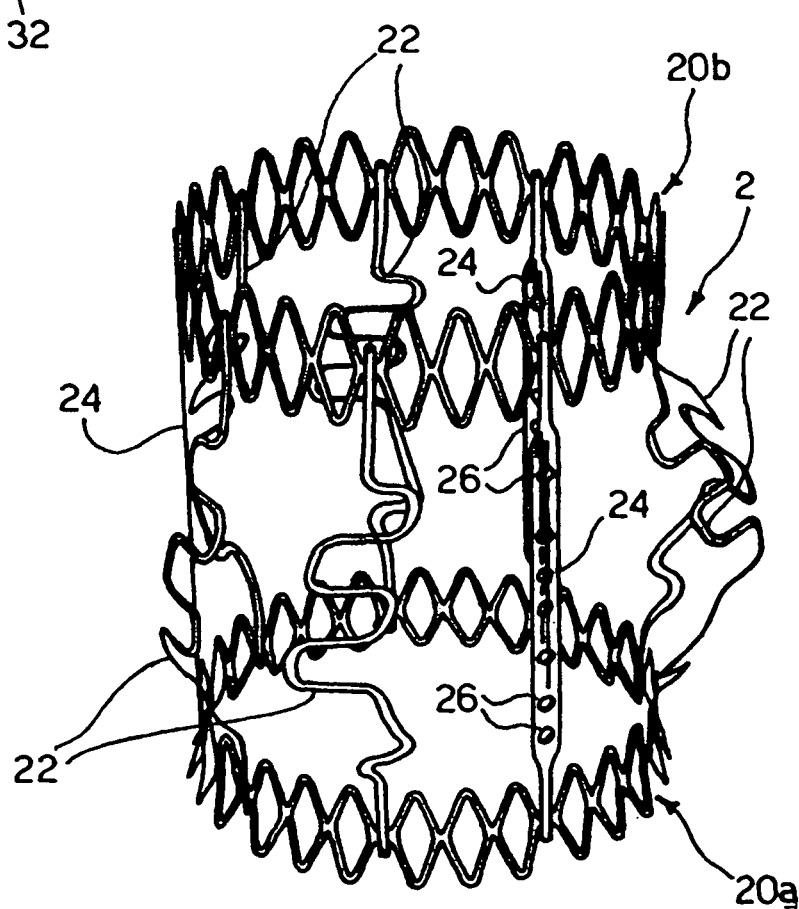

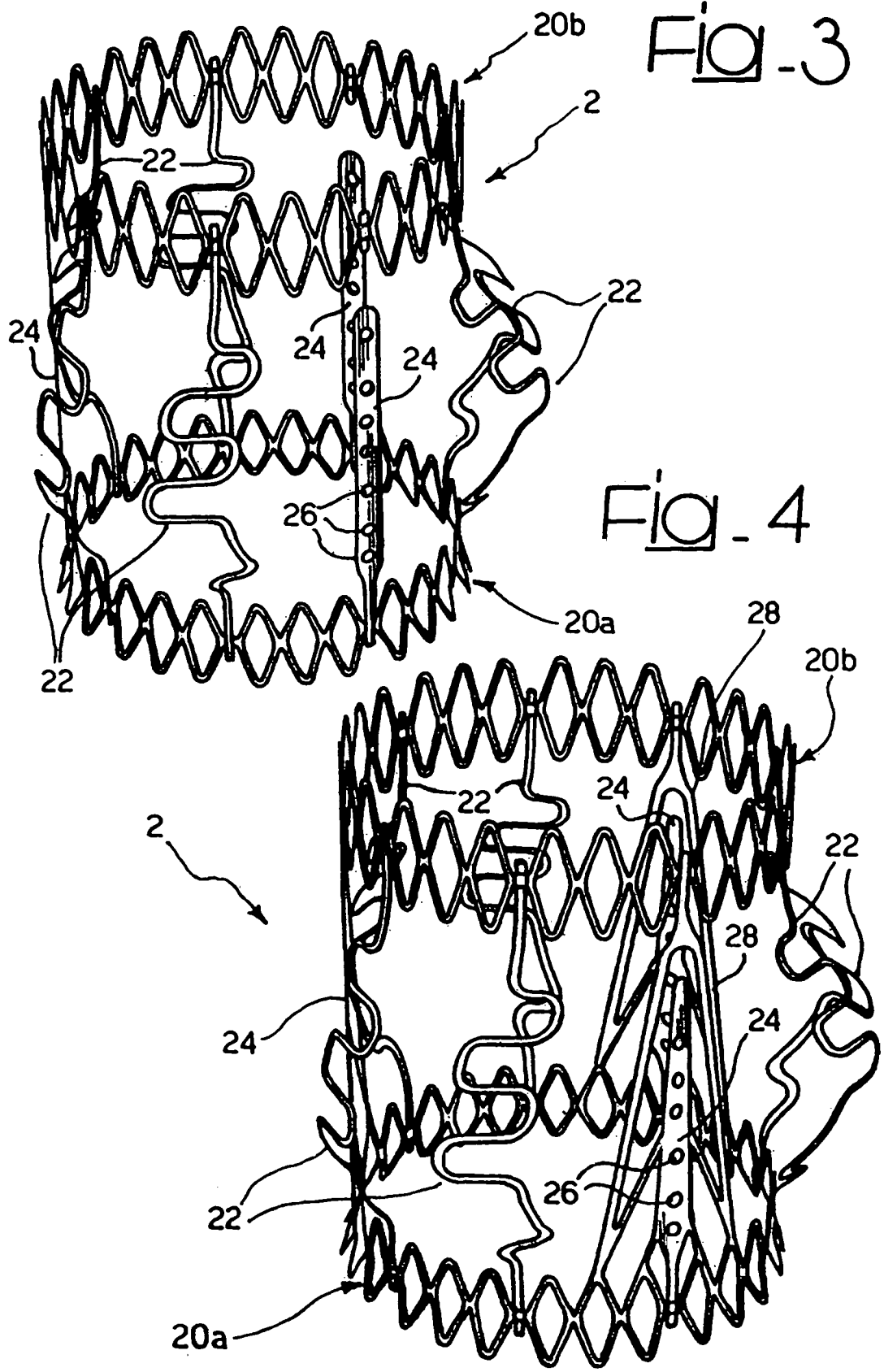

CARDIAC-VALVE PROSTHESIS

CROSS REFERENCE TO RELATED APPLICATION

This application is related to co-pending U.S. patent application Ser. No. 11/066,346 entitled "Minimally-Invasive Cardiac-Valve Prosthesis," and claims priority from Italian patent application number TO2005/A000074, filed on Feb. 10, 2005. Each of the above-identified applications is hereby incorporated by reference for all purposes.

TECHNICAL FIELD

The present invention relates to cardiac-valve prostheses. More specifically, the present invention is directed to a prosthesis that is amenable to a minimally-invasive implantation.

BACKGROUND

Recently, there has been increasing consideration given to the possibility of using, as an alternative to traditional cardiac-valve prostheses, valves designed to be implanted using minimally-invasive surgical techniques or endovascular delivery (the so-called "percutaneous valves"). Implantation of a percutaneous valve (or implantation using thoracic-microsurgery techniques) is a far less invasive act than the surgical operation required for implanting traditional cardiac-valve prostheses. Further details of exemplary percutaneous implantation techniques are provided in U.S. Publication 2002/0042651, U.S. Pat. No. 3,671,979, and U.S. Pat. No. 5,954,766, which are hereby incorporated by reference.

These prosthetic valves typically include an anchoring structure, which is able to support and fix the valve prosthesis in the implantation position, and prosthetic valve elements, generally in the form of leaflets or flaps, which are stably connected to the anchoring structure and are able to regulate blood flow.

Furthermore, the methods of implantation of valves via a percutaneous route or by means of thoracic microsurgery are very frequently irrespective of the effective removal of the natural valve leaflets. Instead, the cardiac valve may be introduced in a position corresponding to the natural annulus and deployed in situ by simply divaricating definitively the natural valve leaflets.

There is a need for a percutaneous valve that does not run the risk of being displaced (dislodged) with respect to the implantation position, as a result of the hydraulic thrust exerted by the blood flow. There is a further need for a percutaneous valve that secures tightly to the flow duct generally defined by the natural valve annulus, such that it resists blood flow around the outside of the percutaneous valve structure.

SUMMARY

In an exemplary embodiment, a cardiac valve prosthesis according to the invention is made so that the entire armature of the valve, or at least the anchorage parts, adhere to the native walls of the implantation site, without interfering with the blood flow, which thus remains practically free. In a preferred way, the anchorage portions moreover have appropriate slits that prevent their interference with the coronary ostia. The anchorage portions and the portions of functional support of the armature can constitute either different parts of a single structure or parts that are structurally distinct from one another. Super-elastic materials can be used in order to obtain a structure that is able to be collapsed for advancement to its implantation site, and to self-recover its expanded geometry once the prosthesis is deployed in the implantation position. The entire armature of the valve, or at least the anchorage parts, can be made even of re-absorbable material, whereas the valve leaflets can be made of biological and/or synthetic tissues, in part colonizable or re-absorbable. In this way, it is possible to obtain anchorage of the device during the period necessary for integration of the valve prosthesis with the physiological tissues of the anatomical site of implantation. Subsequently, there is dissolution of the artificial structure that enables initial anchorage. Amongst the various advantages linked to this solution to be emphasized is the creation of the ideal conditions for a possible prosthetic re-implantation. The armature can include anchorage formations or portions of the supporting structure of the valve flaps made at least partially of shape-memory material (e.g., Nitinol) that enable creation or regulation of the anchorage, i.e., regulation of the modalities and the magnitude of splaying-out of the valve leaflets through control of the memory of the shape-memory material (e.g., by controlling its temperature), according to a mechanism similar to what is described in the document No. EP-A-1 088 529.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

The invention will now be described, purely by way of non-limiting example, with reference to the annexed plate of drawings, in which:

FIG. 1 is a general perspective view of a cardiac-valve prosthesis according to one embodiment of the present invention;

FIGS. 2 to 7 illustrate different embodiments of an armature portion of the cardiac valve prosthesis according to the present invention;

Figure 5:
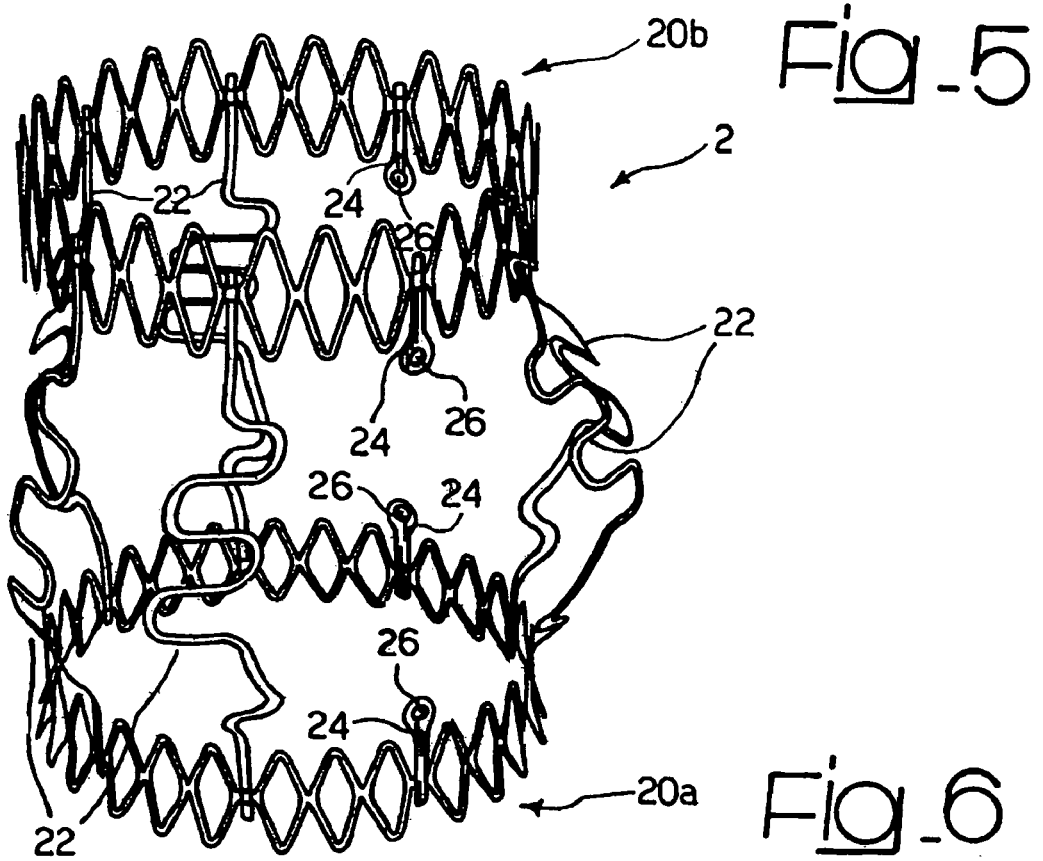

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the figures of the annexed plate of drawings, the reference number 1 designates as a whole a cardiac-valve prosthesis, which can be implanted percutaneously or resorting to techniques of thoracic microsurgery, or else of implantation of a "sutureless" type. Essentially, the prosthesis 1 represented in FIG. 1 includes an armature 2, having the characteristics that emerge more clearly from the representation of FIGS. 2 to 7, and a valve sleeve 3 coupled to the armature 2 and including three valve leaflets 3a, 3b, 3c.

As illustrated in FIG. 2, the armature 2 of the prosthesis 1 can have a general cage-like structure, with a general symmetry of a cylindrical type about a principal axis X1. In percutaneous valves the axis X1 is designed to correspond usually to the principal axis of the distal part of the catheter used for implantation of the prosthesis 1. For the present purpose, the axis X1 can be viewed basically as an entity of a purely geometrical nature. As shown, the armature 2 defines a lumen which operates as a flow tube or duct to accommodate the flow of blood there through. As will be readily apparent to those skilled in the art, a major characteristic of the present invention is the absence of structural elements that can extend in the lumen through which blood flows.

The valve sleeve 3 may be constructed according to various techniques known in the art. For example, techniques for the formation of the valve leaflets, assembly of the valve sleeve and installation thereof on an armature that can be used in the context of the present invention are described in EP-A-0 133 420, EP-A-0 155 245 and EP-A-0 515 324 (all of which are hereby incorporated by reference), the latter document referring to the construction of a cardiac-valve prosthesis of biological tissue of the type commonly referred to as "stentless."

As further illustrated, the valve sleeve 3 includes a base portion 30 with an overall annular pattern, designed to extend from the lower portion of the prosthesis 1, which, in the implantation site, is in a position proximal with respect to the direction of flow of the blood through the prosthesis (from below upwards, as viewed in FIG. 1). Starting from the base portion 30, there extend in an axial direction towards the inside of the structure of the prosthesis 1 three pleat formations 32. The valve leaflets 3a, 3b and 3c extend like a festoon, with a general claw-like conformation, between pairs of pleat formations 32 adjacent to one another.

As illustrated in FIG. 1, each valve leaflet 3a, 3b and 3c has a fluidodynamically proximal edge with an arched pattern, which extends from the base formation 30 and along two adjacent pleat formations 32, and a fluidodynamically distal edge, which extends towards the central orifice of the prosthesis so as to be able to co-operate with the homologous edges of the other valve leaflets. The terms "fluidodynamically proximal" and "fluidodynamically distal" refer to the direction of free flow of the blood through the prosthesis, a direction that is from below upwards, as viewed in the figures of the annexed plate of drawings.

As will be understood by those of ordinary skill in the art, in operation, the valve leaflets 3a, 3b, 3c are able to undergo deformation, divaricating and moving up against the armature 2 so as to enable free flow of the blood through the prosthesis. When the pressure gradient, and hence the direction of flow, of the blood through the prosthesis tends to be reversed, the valve leaflets 3a, 3b, 3c then move into the position represented in FIG. 1, in which they substantially prevent the flow of the blood through the prosthesis. Usually, the valve leaflets 3a, 3b, 3c are made in such a way as to assume spontaneously, in the absence of external stresses, the closed configuration represented in FIG. 1.

FIGS. 2 through 7 depict the armature 2 according to various embodiments of the present invention. Referring first to FIG. 2, it is shown that the armature 2 (which may be made of metal material, such as for example the material commonly referred to as Nitinol) includes two annular elements 20a, 20b, which generally occupy respective end positions within the armature 2. In one embodiment, in the site of implantation of the prosthesis 1, the annular elements 20a and 20b are designed to be located, respectively, upstream and downstream of the sinuses of Valsalva.

During implantation, the prosthesis 1 is advanced towards the implantation site in a radially contracted configuration, with the annular elements 20a and 20b in a radially collapsed configuration. In one embodiment, when so collapsed, the annular elements 20a, 20b have a minimum diameter of about 5 to about 15 mm, according to the technique of implantation for which the prosthesis is designed. Once the prosthesis 1 has reached the implantation site, the annular elements 20a, 20b are made/allowed to expand until they reach their normal expanded configuration, with a diameter that ranges, in one embodiment, from about 18 to about 30 mm.

In order to enable the movement of expansion, the annular elements 20a and 20b are made, according to the illustrated embodiment, with a mesh structure substantially resembling the mesh structure of a stent for angioplasty. It will be appreciated in fact that the annular elements 20a and 20b are designed to perform a movement of radial expansion (with subsequent maintenance of the radially expanded configuration) substantially resembling the movement of expansion in situ of an angioplasty stent.

In the example of embodiment illustrated herein, the annular elements 20a and 20b have a rhomboidal-mesh structure. In other embodiments, the parts 20a, 20b can be made with any structure that is able to ensure the necessary functionality.

In one embodiment, as shown in FIG. 2, the annular element 20a designed to be located in a position proximal with respect to the flow of the blood through the prosthesis 1 (i.e., on the inflow side of the blood in the prosthesis 1 in the conditions of free flow) may have a proximal end that is at least slightly flared outward like an enlarged opening of the flow duct of the blood. This configuration functions to promote a more positive anchorage of the annular element 20a, and in turn, the prosthesis 1, to the valve annulus, thus promoting the perivalvar tightness, improving the haemodynamics, and adapting (i.e., radiusing) the lines of blood flow in the ventricular chamber to the flow tube constituted by the valve sleeve.

As shown, the annular elements 20a, 20b are connected to one another by anchor members 22, which in the illustrated embodiment, are generally arched, projecting towards the outside of the prosthesis 1. In one embodiment, the anchor members 22 are designed such that when the prosthesis 1 is positioned at the implantation site, the anchor members 22 can extend on the outside of the sinuses of Valsalva so as to ensure firm anchorage in situ of the prosthesis 1.

With the prosthesis 1 in the radially contracted configuration adopted for implantation, the anchor members 22 are normally maintained in a position (not shown) recalled towards the central axis X1 of the prosthesis 1. This can occur, for example, via a retention means such as a tubular sheath of an implantation catheter through which the radially contracted prosthesis is advanced. Subsequently, once disengaged from the retention means, the anchor members 22 may assume the arched pattern represented in the figures so as to be able to project (protrude), in one embodiment, within the sinuses of Valsalva.

As will be appreciated by those skilled in the art, the sinuses of Valsalva are, in a normal heart, three in number, and are distributed in an approximately angularly uniform way around the root of the artery distal to the semilunar valve (i.e., the aortic or pulmonary valve). Accordingly, as illustrated, the prosthesis 1 may include three anchor members 22 (or three groups of anchor members) set at an angular distance apart of about 120° with respect to the central axis X1 of the prosthesis.

In the exemplary embodiment illustrated, the anchor members 22 are made in the form of ribbon-like elements that extend in a generally sinusoidal or serpentine path, with bends or open loops situated on either side with respect to an ideal line extending approximately in the direction of the generatrices of the overall cylindrical shape of the prosthesis. In another embodiment of the invention, the sinusoidal pattern can be obtained with bends or open loops that extend from one side and from the other with respect to a line that extends in a circumferential direction with respect to the prosthesis. In yet another embodiment, the anchor members 22 may have a mesh structure, for example closed rhomboidal meshes of the same type as the one represented with reference to the annular elements 20a, 20b, or to simple segments of curve lying in roughly radial planes. Additionally, as discussed above, each anchor member 22 can consist either of a single element or of a plurality of elements (e.g., pairs of anchor members 22 as shown in FIGS. 2-7) that extend in a direction in which they are generally set alongside one another.

The annular elements 20a and 20b and the respective anchor members 22 substantially form the basic structure of the armature 2 of the prosthesis 1, which is designed to ensure positioning and anchorage in situ of the prosthesis 1 itself.

Associated then to the annular elements 20a and 20b are further support members, generically designated by 24 in all of FIGS. 2 to 7, which operate to support the valve sleeve 3 on the armature 2 of the prosthesis 1. In the embodiment represented in FIG. 2, the support members 24 are simply represented by three generally flat bars extending between and connecting the annular members 20a, 20b. As further illustrated, the support members 24 are set at an angular distance apart of about 120°, with each generally located at a position that is approximately centrally intermediate the anchor members 22.

As may be appreciated from a comparative examination of FIGS. 1 and 2, the support members 24 are designed to enable the installation of the valve sleeve 3 in a condition such that the base portion 30 thereof is arranged in general in a position around the annular element 20a of the armature 2, while each of the pleat formations or folds 32 in turn embraces one of the elements or support members 24, while the valve leaflets 3a, 3b and 3c extend in a festoon, each between two adjacent support members 24. The general apertured structure both of the annular element 20a and of the support members 24 (note the particular holes designated by 26) enables fixing of the valve sleeve 3 on the armature 2 by, for example, suturing stitches according to known techniques. In the case where flaps of polymeric materials are used, the flaps can be formed directly on the structure, using techniques such as, for example, dip casting.

In this regard, both the armature 2 and the aforesaid suturing stitches can be advantageously provided with a coating of biocompatible carbon material, which may be applied according to the solutions described in U.S. Pat. Nos. 4,624, 822, 4,758,151, 5,084,151, 5,133,845, 5,370,684, 5,387,247, and 5,423,886, the contents of which are hereby incorporated by reference.

The apertured structure of the supporting formations 24, and of the armature 2 in general, means that the armature 2 does not exert any substantial obtrusive effect, preventing, for example, interference in regard to the coronary ostia.

FIG. 3 depicts an alternative embodiment of the armature 2 of the present invention. The variant embodiment represented in FIG. 3 as a whole resembles the embodiment represented in FIG. 2, with the exception that (in the embodiment of FIG. 3) the support members 24 provided for anchorage of the valve sleeve 3 do not extend completely in bridge-like fashion between the two annular parts 20a and 20b. Rather, in the embodiment illustrated in FIG. 3, the support members 24 are projecting elements that extend in cantilever fashion starting from the annular element 20a, and do not reach the annular element 20b. In particular, the lengths of the aforesaid cantilevered support members 24 are determined in such a way as to extend for a length sufficient to enable anchorage of the valve sleeve 3 to the support members 24 at the pleat formations 32. Thus, in one embodiment, the support members 24 do not include any portions other than those portions which operate to support the valve sleeve 3.

FIG. 4 illustrates another embodiment of the armature 2 according to the present invention. As shown, in the embodiment of FIG. 4, like that shown in FIG. 3, the support members 24 project in cantilever fashion from the annular element 20a. As further shown in FIG. 4, in this embodiment, the support members 24 have associated thereto fork-like structures 28. Each fork-like structure 28 has a root portion connected to the annular element 20b and two prongs that extend on either side of the respective support member 24 and then connect up to the annular element 20a on opposite sides with respect to the area in which the support member 24 projects in cantilever fashion from the formation 20a.

As further shown in FIG. 4, in one embodiment, the support members 24 are generally tapered, such that they have widths that decrease gradually moving away from the annular element 20a, that is, in the proximal-to-distal direction with reference to the direction of free flow of the blood through the prosthesis. As will be apparent to those skilled in the art, tapering of the support members 24 may be employed in any of the embodiments illustrated in FIGS. 2 to 4. Similarly, any of the other characteristics of the support members 24 or the anchor members 22, which albeit herein represented are identical to one another in each of the embodiments illustrated, could in actual fact be different from one another. That is, in any embodiment of the valve prosthesis 1, there could coexist, in a single prosthesis, anchor members 22 or support members 24 different from one another, with characteristics drawn from different embodiments amongst the plurality of embodiments illustrated herein.

The solution represented in FIG. 4 generally provides a more rigid anchorage structure as compared to the embodiment of FIG. 3. In the embodiment illustrated in FIG. 4, the fork-like formations 24 effectively fix the axial dimension of the prosthesis 1, which promotes the expansion of the anchor members 22 in the sinuses of Valsalva. At the same time, in the illustrated embodiment of FIG. 4, the support members 24, which operate to facilitate attachment of the valve sleeve 3 to the armature 2, are maintained flexible and of modulatable stiffness.

In the embodiment represented in FIG. 5, the support members 24 are provided in positions corresponding to both of the annular elements 20a, 20b. In this case, however, the support members 24 provided for anchorage of the valve sleeve 3 are reduced to small hooking cantilevers, each provided with an eyelet 26. The eyelets 26 can be used directly for passing and tying the wires that extend from the valve sleeve 30.

Figure 6:
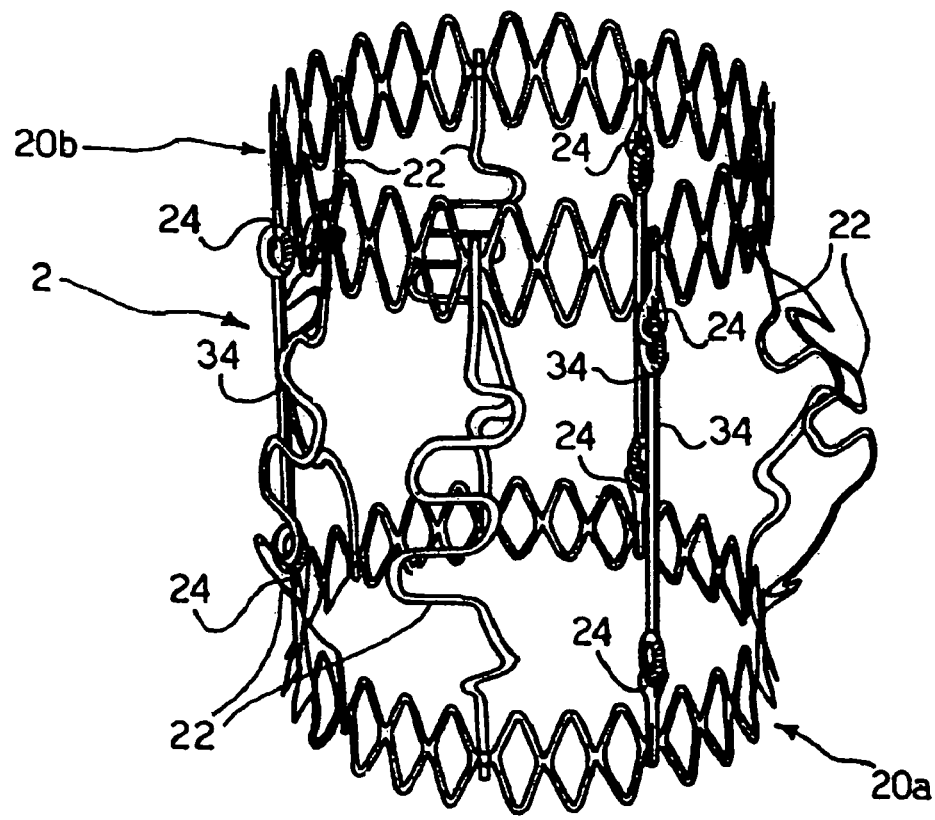

Yet another embodiment is shown in FIG. 6, in which the support members 24 are arranged in opposed pairs, with each of the support members 24 within a pair extending in cantilever fashion from one of the annular elements 20a, 20b and being connected by a connecting element 34. In one embodiment, the connecting elements 34 may have a generally filiform (i.e., relatively long and thin) shape, whereby the connecting elements 34 may be made relatively flexible and thus may provide a flexible connection between the support members 24. In one embodiment, the connecting elements 34 may be made from biocompatible metal alloys (e.g., Nitinol) or polymeric materials suitable for applications in the field of implantations (e.g., acetal resins).

As shown, the overall configuration of the embodiment of FIG. 6 generally resembles, from a geometrical standpoint, the embodiment represented in FIG. 2. The difference lies in the fact that, whereas the support members 24 represented in FIG. 2 are as a whole generally stiff (taking into account the intrinsic flexibility of the material that constitutes them), the connecting elements 34 shown in FIG. 6 may have a filiform shape with a relatively high flexibility. The embodiment illustrated in FIG. 6 thus enables the configuration for hooking of the valve sleeve 3 to the armature 2 of the prosthesis to be rendered elastic/flexible and renders the extent of the anchor members 22 independent of that of the support members 24, thus enabling a greater elasticity of design.

Figure 7:
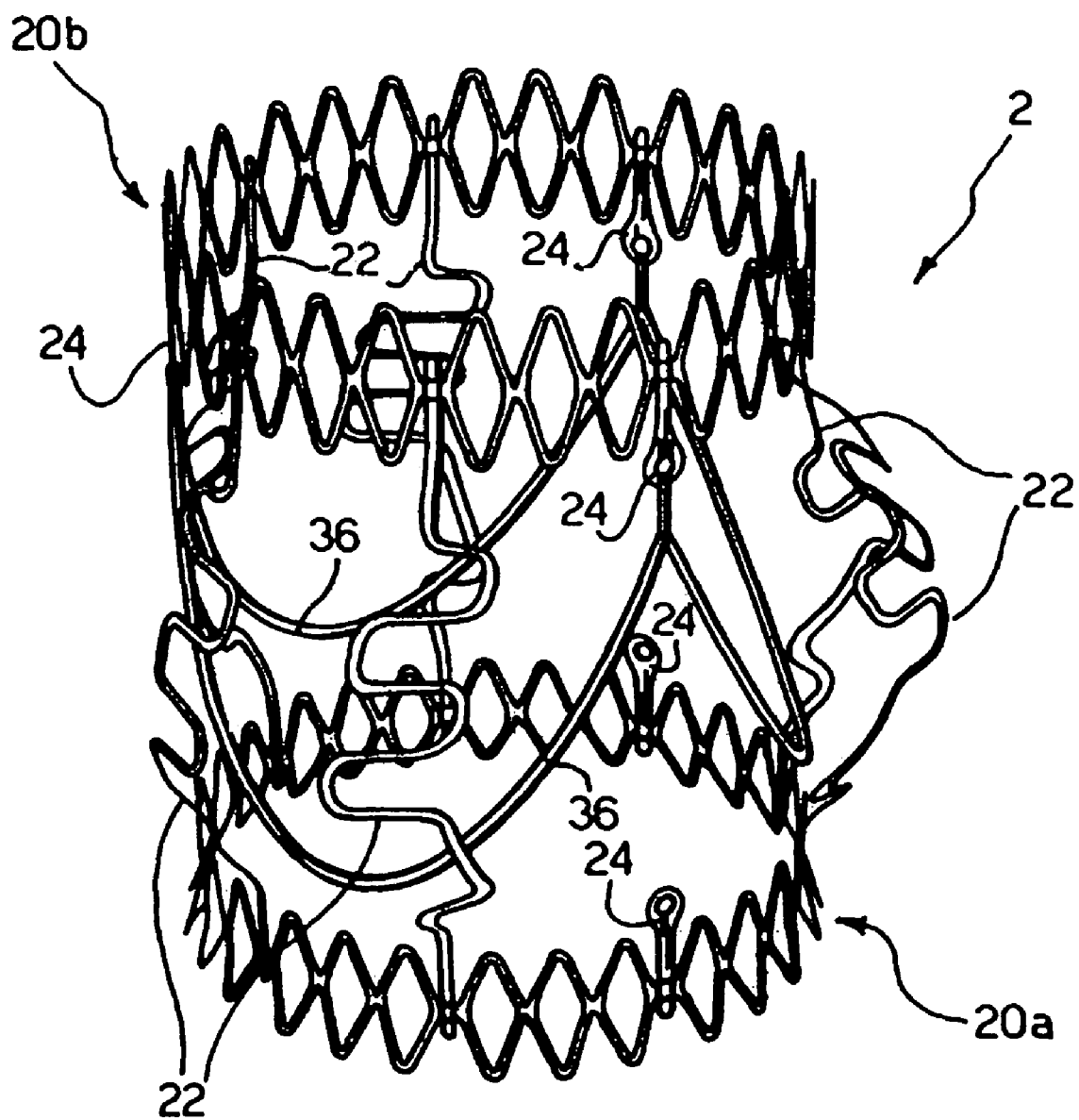

FIG. 7 depicts yet another embodiment of the armature 2, which is otherwise similar to the embodiment illustrated in FIG. 6, except that in the embodiment of FIG. 7, the mutually facing pairs of support members 24 are not connected to each other (as by the connecting members 34 in FIG. 6). Instead, in the embodiment represented in FIG. 7, a supporting element 36 extends between and connects each of the support members 24 extending in cantilever fashion from the annular element 20b. As shown, the supporting elements 36 may extend in a generally festoon-like or catenary path between each of the support members 24 attached to the annular part 20b. The supporting elements 36 are configured such that each can support one of the valve leaflets 3a, 3b, or 3c of the valve sleeve 3. The supporting elements 36 may be made of substantially rigid or flexible materials.

In another embodiment (not shown), the supporting elements 36 may be configured to extend from the support members 24 extending in cantilever fashion from the annular element 20a.

As will be readily understood by those skilled in the art, festoon-like or catenary pattern of the supporting elements 36 may be generally configured to match the homologous pattern of the proximal edges of the valve leaflets 3a, 3b and 3c (see FIG. 1), defining the profile of the edge for anchorage of the functional flaps and, possibly, enabling connection by suture of the aforesaid proximal edges of the valve leaflets to the festoon-like supporting elements 36. This enables the use of relatively simple valve sleeves 3, assigning the formation of the profile of the functional flaps of the valves to the supporting elements 36.

The embodiments of the present invention described herein enables, in the final position of implantation, the entire armature 2 of the prosthesis 1, or at least the anchorage parts, to adhere to the native walls of the implantation site, without interfering with the blood flow, which thus remains practically free. Additionally, the armature 2 and anchor members 22 moreover have a generally apertured structure (for example, appropriate slits), which prevents interference with the coronary ostia.

The anchorage portions and the portions of functional support of the armature 2 can constitute either different parts of a single structure or parts that are structurally distinct from one another. The entire armature 2, or at least the anchorage parts (e.g., the anchor members 22), may be made of re-absorbable material, whereas the valve sleeve 3 can be constituted by biological and/or synthetic tissues, which are in part colonizable or re-absorbable.

Alternatively, as discussed above, the armature 2 can contain anchorage formations (e.g., anchor members 22) made at least partially of shape-memory material (e.g., Nitinol), which enable creation or regulation of the anchorage through the control of the memory of the shape-memory material (e.g., controlling its temperature).

Figure 8:
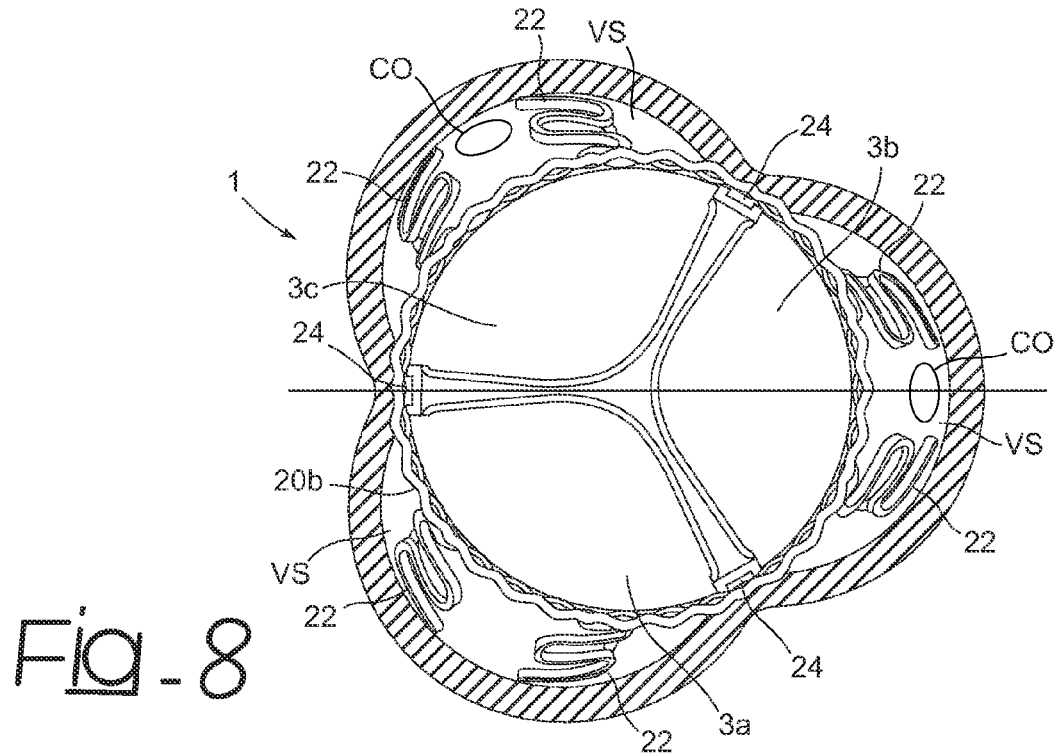
FIGS. 8 and 9 illustrate plan and cross-sectional views, respectively, of the cardiac valve prosthesis implanted at an implantation site in a patient, according to an embodiment of the present invention.
Figure 9:
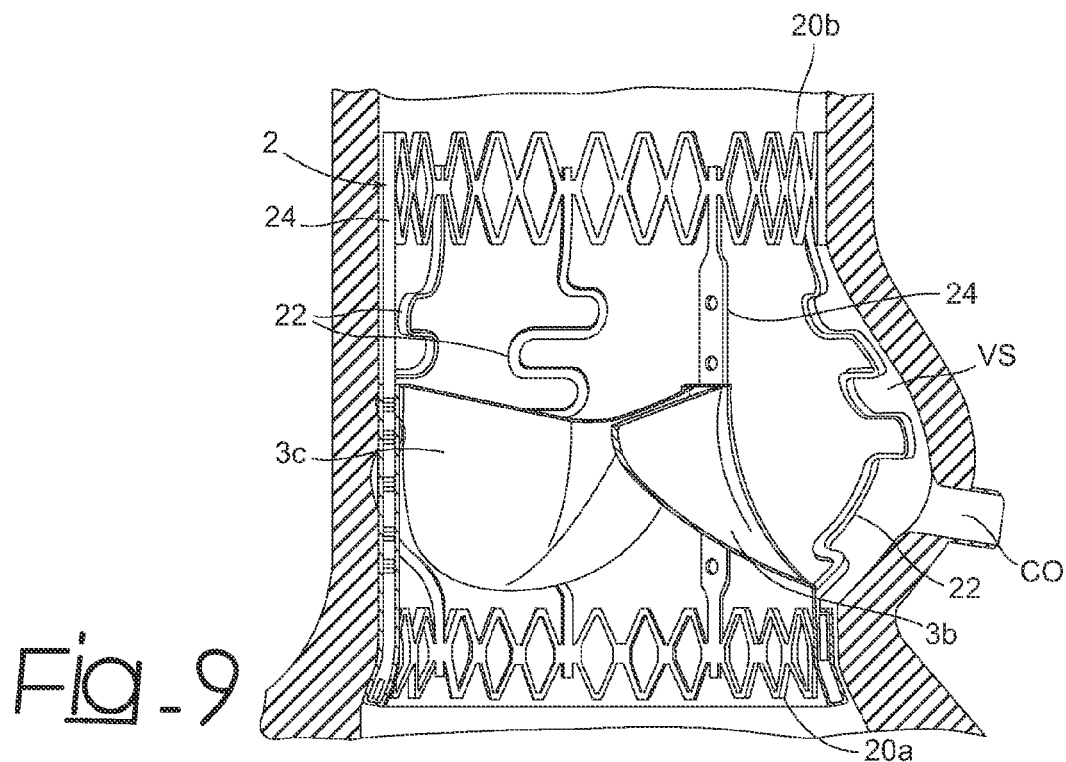

FIGS. 8 and 9 illustrate plan and cross-sectional views, respectively, of the prosthesis 1 in its implanted state in an aortic valve replacement, according to an embodiment of the invention. As shown, and as discussed in detail above, the prosthesis 1 can be implanted such that the annular elements 20a and 20b occupy positions proximal and distal, respectively, of the Valsalva sinuses VS, with the flared proximal end of the annular member 20a forming the proximal entrance of the lumen defined by the armature 2 of the prosthesis 1. In the illustrated embodiment, the anchor members 22 can be arranged in three pairs positioned relative to the sinuses of Valsalva such that the radially projecting portion of each of the anchor members 22 projects into the respective sinus of Valsalva and engages the aortic wall therein. As further shown, the anchor members 22 of each pair can be positioned on opposite sides of the coronary ostia CO in the respective sinuses of Valsalva. Additionally, as discussed above and shown in FIGS. 8 and 9, the serpentine or otherwise generally apertured structure of the anchor members 22 substantially avoids interference with the coronary ostia CO. Finally, as can be seen from FIGS. 8 and 9, the valve leaflets 3a, 3b, 3c can be positioned within the lumen for blood flow formed by the annular elements 20a, 20b, with the support members 24 extending into the lumen by a minimal amount.

The armature 2 of the prosthesis 1, according to one embodiment, is manufactured by first cutting a blank part from a tube of a biocompatible metal (e.g., Nitinol, or a cobaltum-chromium alloy) having an outer diameter which is at an intermediate size between the fully radially contracted and the fully expanded device dimensions. For example, the tube may have an outer diameter of between about 8 mm to about 14 mm. In one embodiment, the tube has a diameter of about 10 mm. In one embodiment, the tube wall may vary between about 0.3 mm to about 0.5 mm, depending on the required stiffness required and the size of the prosthesis 1.

In one embodiment, the final dimension and shape of the framework is achieved by a sequence of expansion cycles. A specific heat treatment is applied after each expansion cycle to homogenize and stress relieve the material, which allows the shape and properties of the structure of the armature 2 to be set. Although the number of forming steps may vary among devices, for the geometries described above with respect to the present invention, and using Nitinol for the tube blank, an exemplary number of forming steps is around three. Among these steps, the first two provide the final diameter of the annular elements 20a, 20b. For example, if the fully-expanded diameter for implantation is 23 mm, the final cylindrical shape of the armature 2 can be achieved using a tube blank of about 10 mm in diameter, a first expansion from about 10 mm to about 18 mm, and a second expansion from about 18 mm to about 23 mm. Optionally, the final diameter can be made slightly larger (e.g. about 25 mm in the previous example) in order to oversize the armature 2 with respect to the physiological annulus, thus imparting a radial force to the wall of the annulus at the nominal implant diameter.

The third forming step is aimed to impart the radially extending shape of the anchor members 22 such that they will fit and anchor within the Valsalva sinuses. The corresponding heat treatment, according to one embodiment, includes exposing the deformed armature 2 to a temperature from about 480° C. to about 550° C., for a time ranging from about 5 minutes to about 30 minutes, depending on the desired final transformation temperature. For example, in order to obtain a super-elastic behavior at 37° C. (the normal working condition in human body) the heat treatments subsequent to the two initial expansion steps may be performed at about 480° C. for a time of about 9 minutes, and the final heat treatment (after the third expansion) is performed at about 500° C. for a time of about 9 minutes.

After the forming process is complete, the armature 2 may undergo one or more surface treatments, for example, sandblasting and electropolishing, to provide a sufficiently smooth surface and to remove the shallow defects. The armature 2 may thereafter be finally exposed to a carbon coating process in order to improve its hemocompatibility.

As shown in FIGS. 8-9, for an aortic valve replacement, the final geometrical shape of the armature 2 will generally approximate the physiological shape and dimension of the aortic root, such that the anchor members 22 generally conform to the walls of the respective Valsalva sinuses VS.

Figure 10:
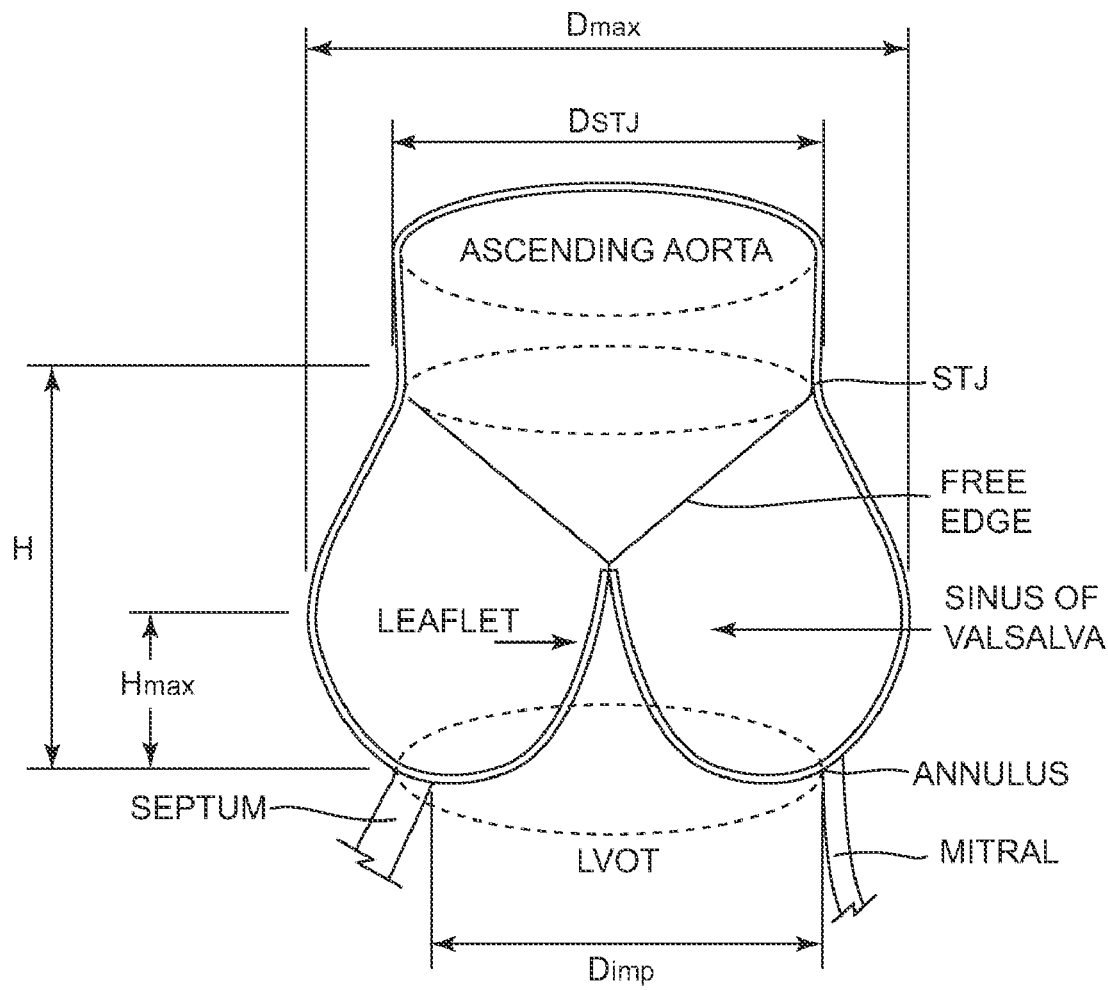
FIG. 10 is a schematic cross-sectional view of an implantation site for the cardiac valve prosthesis according to one embodiment of the present invention.

FIG. 10 shows a schematic cross sectional view of an implantation site for an aortic valve replacement. Referring to FIG. 10, exemplary proportions of the relevant features at the implantation site for an aortic valve replacement are as follows (assuming the annulus diameter $D_{imp}$ (implanting diameter) equal to 1):

|  | Approximate Minimum | Approximate Maximum |
| --- | --- | --- |
| Height of Valsalva sinuses (H): | 0.8 | 1 |
| Max. diameter of Valsalva sinuses (Dmax): | 1.3 | 1.7 |
| Distance between Valsalva max. diameter and basic annulus plane (Hmax): | 0.3 | 0.5 |
| Diameter at the sino-tubular junction (Dstj): | 0.8 | 1.4 |

According to one exemplary embodiment, H is about 0.9, Dmax is about 1.5, Hmax is about 0.35, and Dstj is about 1.2.

The commissural points of the elastic collapsible valve 3 are mounted to the armature 2 (e.g., by attachment to the support members 24) such that the valve leaflets 3a, 3b, and 3c can fold and expand together. The valve 3, including the valve leaflets 3a, 3b, 3c, can be, for example, a glutaraldehyde fixed pericardium valve which has three cusps that open distally to permit unidirectional blood flow.

In one embodiment, the valve member may use two pericardium sheets. The first sheet forms the three moving cusps, the second sheet coats part of the armature 2 surface so that there is no contact between the armature 2 and the valve leaflets avoiding the risk of abrasion due to repeated impact against the metallic material of the armature 2. In addition, this second sheet redistributes the stress applied by blood pressure on the prosthetic leaflets, avoiding the risk of stress concentration.

The two sheets of pericardium may be stitched together flat using suture thread coated with a film of biocompatible material, and then close in a cylindrical shape. The type of stitch used may be varied to accommodate the directional differences in the forces exerted at each point of the suture, to ensure that the stitches themselves don't become the origin of fatigue fracture lines. The two sheets may be stitched together in a flat position so when the leaflets open they recover their original cylindrical configuration, forming a cylindrical duct.

The elastically collapsible valve sleeve 3 can be mounted on the armature 2 by means of a number of suture stitches. Both of the sheets are useful for attaching the valve sleeve 3 to the armature 2 by stitching.

The valve member can use a tissue fixation and shaping of the leaflets 3a, 3b, 3c by means of a fluidic, atraumatic system with chemicals useful for cross-linking and then may be exposed to a detoxification post treatment to increase long-term performance. An additional pericardium sheet corresponding to base portion 30 of the valve sleeve 3 can be positioned in a generally cylindrical fashion around the annular element 20a so as to improve the sealing capability of the prosthesis 1 to the valve annulus.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A cardiac valve prosthesis adapted for implantation at an implantation site of a patient, the implantation site having an annulus, a plurality of Valsalva sinuses, coronary ostia, and a vessel wall distal to the Valsalva sinuses, the prosthesis having a principal axis extending longitudinally therethrough and comprising:

an armature adapted for delivery in a radially collapsed configuration and deployment in a radially expanded configuration, the armature defining a lumen for passage of blood flow and comprising:

first and second annular elements positioned about the principal axis, the first annular element adapted to engage a wall of the annulus proximal to the Valsalva sinus and the second annular element adapted to engage the vessel wall distal to the Valsalva sinus;

a plurality of anchor members extending from the first annular element to the second annular element, each anchor member arching radially outward with respect to the annular elements such that the anchor member is adapted to extend into and generally conform to a respective one of the Valsalva sinuses between the first and second annular elements to enable anchorage of the prosthesis at the implantation site when the cardiac valve prosthesis is deployed at the implantation site with the armature in the radially expanded configuration; and a plurality of valve support members connected to and extending between the first and second annular elements and oriented generally parallel to the principal axis of the prosthesis, wherein each of the valve support members and each of the anchor members are angularly spaced from one another around the principal axis; and a set of prosthetic valve leaflets coupled to the valve support members.

2. The prosthesis of claim 1 wherein the armature comprises three anchor members angularly distributed around the prosthesis such that each anchor member can extend into a respective Valsalva sinus.

3. The prosthesis of claim 2 wherein each of the anchor members has a generally serpentine shape.

4. The prosthesis of claim 2 wherein each of the annular elements is made from a shape memory material.

5. The prosthesis of claim 2 wherein the anchor members are made from a shape memory material.

6. The prosthesis of claim 2 wherein the anchor members are made substantially from a re-absorbable material.

7. The prosthesis of claim 1 wherein each of the annular elements has a mesh structure.

8. The prosthesis of claim 7 wherein each of the annular elements has a rhomboidal-mesh structure.

9. The prosthesis of claim 1 wherein at least one of the annular elements is flared outward at a proximal end.

10. The prosthesis of claim 1 wherein at least one of the support members comprises a plurality of apertures.

11. The prosthesis of claim 1 wherein the at least one of the support members has a tapered pattern.

12. The prosthesis of claim 11 wherein the at least one of the support members has a width that decreases in the proximal-to-distal direction.

13. The prosthesis of claim 1 wherein the valve leaflets are made substantially of materials selected from the group consisting of biological tissues, colonizable tissues, and re-absorbable tissues.

14. A cardiac valve prosthesis for implantation at an implantation site of a patient, the prosthesis having a principal axis extending longitudinally therethrough and comprising:
an anchoring structure having a collapsed configuration and an expanded configuration, the anchoring structure defining a lumen;
a valve coupled to the anchoring structure and configured such that in the expanded configuration, the valve permits blood flow through the lumen in a first direction and substantially prevents blood flow through the lumen in a second direction opposite the first direction,
wherein the anchoring structure includes a first generally cylindrical portion positioned about the principal axis adapted to engage an annular wall of the implantation site proximal to a Valsalva sinus, a second generally cylindrical portion positioned about the principal axis adapted to engage a vessel wall distal to the Valsalva sinus, Valsalva sinus anchoring means for anchoring the prosthesis at the implantation site, the Valsalva sinus anchoring means connected to and extending between the first and second generally cylindrical portions and arching radially outwardly with respect to the first and second generally cylindrical portions for generally conforming to and engaging a wall of the Valsalva sinus of the implantation site between the first generally cylindrical portion and the second generally cylindrical portion, and a plurality of valve support members connected to and extending between the first and second generally cylindrical portions in a direction generally parallel to the principal axis of the prosthesis, wherein each of the valve support members and the Valsalva sinus anchoring means are angularly spaced from one another about the principal axis of the prosthesis.

15. The prosthesis of claim 14 wherein the first or second generally cylindrical portion has a mesh structure.

16. The prosthesis of claim 15 wherein the first or second generally cylindrical portion has a rhomboidal-mesh structure.

17. The prosthesis of claim 14 wherein the first or second generally cylindrical portion is made from a shape memory material.

18. The prosthesis of claim 14 wherein the means for anchoring are made from a shape memory material.

19. A method for percutaneous implantation of a cardiac valve prosthesis at an implantation site having an annulus and a Valsalva sinus having a wall and a coronary ostia, the prosthesis having a principal axis extending longitudinally therethrough, the method comprising deploying the prosthesis from a delivery catheter such that a first generally cylindrical portion of the prosthesis positioned about the principal axis engages a wall of the annulus, a second generally cylindrical second portion of the prosthesis positioned about the principal axis engages a vessel wall distal to the Valsalva sinus, a Valsalva sinus anchor portion of the prosthesis expands to a size and shape arching radially outwardly and conforming to the wall of the Valsalva sinus between the first and second generally cylindrical portions, and a plurality of valve leaflet support members extend between the first and second generally cylindrical portions in a direction generally parallel to the principal axis of the prosthesis, wherein each of the valve leaflet support members and the Valsalva sinus anchor portion are angularly spaced from one another about the principal axis of the prosthesis.

* * * * *